United States Patent
Chen et al.

(10) Patent No.: US 9,348,337 B2
(45) Date of Patent: May 24, 2016

(54) ENVIRONMENT RECOGNITION GUIDE SYSTEM FOR MOVABLE MEDICAL EQUIPMENT AND METHOD

(71) Applicant: SWISSRAY ASIA HEALTHCARE CO., LTD., Taipei (TW)

(72) Inventors: Te Mu Chen, Taipei (TW); Yun Feng Hsieh, Taipei (TW)

(73) Assignee: Swissray Asia Healthcare Co., Ltd., Taipei (TW)

(*) Notice: Subject to any disclaimer, the term of this patent is extended or adjusted under 35 U.S.C. 154(b) by 6 days.

(21) Appl. No.: 14/459,526

(22) Filed: Aug. 14, 2014

(65) Prior Publication Data

US 2015/0331425 A1  Nov. 19, 2015

(30) Foreign Application Priority Data

May 14, 2014 (TW) .............................. 103116937 A
May 14, 2014 (TW) .............................. 103208368 U

(51) Int. Cl.
| | | |
|---|---|---|
| *G05D 1/02* | (2006.01) | |
| *A61B 6/10* | (2006.01) | |
| *A61B 6/00* | (2006.01) | |

(52) U.S. Cl.
CPC .............. *G05D 1/0246* (2013.01); *A61B 6/102* (2013.01); *A61B 6/105* (2013.01); *A61B 6/4405* (2013.01); *A61G 2203/22* (2013.01); *G05B 2219/49143* (2013.01)

(58) Field of Classification Search
CPC ..... G05D 1/00; G05D 1/0246; G05D 1/0251; G05D 1/0253; A61B 6/102
USPC ............................................... 701/23–28, 301
See application file for complete search history.

(56) References Cited

U.S. PATENT DOCUMENTS

| | | | | |
|---|---|---|---|---|
| 7,957,837 B2 * | 6/2011 | Ziegler | ..................... | B25J 5/007 318/568.1 |
| 8,031,060 B2 * | 10/2011 | Hoffberg | ............... | G05B 15/02 340/426.15 |
| 8,543,241 B2 * | 9/2013 | Hong | ..................... | B25J 9/0003 318/568.12 |
| 8,718,837 B2 * | 5/2014 | Wang | ..................... | B25J 9/1689 382/209 |

(Continued)

*Primary Examiner* — Thomas Tarcza
*Assistant Examiner* — Tyler J Lee
(74) *Attorney, Agent, or Firm* — Rosenberg, Klein & Lee

(57) ABSTRACT

An environment recognition guide system and method for guiding a movable medical equipment are disclosed. The environment recognition guide system includes a depth camera, an environment data storage device, and an object image recognition device. When the object image recognition device compares and determines an environment image pixel depth signal acquired by the depth camera matching predetermined object image pixel depth signals stored in the environment data storage device, the medical equipment is driven to move along a preset guide path. The movable medical equipment is further provided with collision protection function to prevent the medical equipment from collision with a front obstacle during the movement.

8 Claims, 7 Drawing Sheets

(56) References Cited

U.S. PATENT DOCUMENTS

| | | | | |
|---|---|---|---|---|
| 8,918,209 B2* | 12/2014 | Rosenstein | ............ | B25J 11/009 700/245 |
| 8,965,579 B2* | 2/2015 | Wang | ............ | B25J 9/1689 700/259 |
| 8,994,776 B2* | 3/2015 | Sutherland | ............ | B25J 5/007 180/167 |
| 9,014,848 B2* | 4/2015 | Farlow | ............ | G05D 1/0246 700/245 |
| 2012/0173018 A1* | 7/2012 | Allen | ............ | B25J 13/06 700/245 |
| 2012/0182392 A1* | 7/2012 | Kearns | ............ | B25J 11/009 348/46 |
| 2012/0185096 A1* | 7/2012 | Rosenstein | ............ | B25J 11/009 700/259 |
| 2013/0123015 A1* | 5/2013 | Jung | ............ | G06K 9/78 463/37 |
| 2014/0022353 A1* | 1/2014 | Hamersma | ............ | A61B 6/102 348/46 |
| 2014/0365060 A1* | 12/2014 | Yamamoto | ............ | G05D 1/02 701/23 |
| 2015/0073646 A1* | 3/2015 | Rosenstein | ............ | B25J 11/009 701/28 |

* cited by examiner

| guide path | objects | predetermined object image pixel depth signals |
|---|---|---|
| L | A1 | S31 |
| | A2 | S32 |
| | A3 | S33 |
| | ⋮ | ⋮ |
| | An | S3n |

| obstacle distance d | control signals | moving modes |
|---|---|---|
| > d1 | Sd1 | normal movement |
| < d2 | Sd2 | slow movement |
| < d3 | Sd3 | stop movement |

FIG.6

ENVIRONMENT RECOGNITION GUIDE SYSTEM FOR MOVABLE MEDICAL EQUIPMENT AND METHOD

BACKGROUND OF THE INVENTION

1. Field of the Invention

The present invention relates to a control system and method of a movable medical equipment, and in particular to a movable medical equipment that is combined with a depth camera, an environment data storage device, and an object image recognition device for driving the medical equipment to move along a predetermined guide path in an environmental space. The movable medical equipment is further provided with collision protection function to prevent the medical equipment from collision with a front obstacle during the movement.

2. The Related Arts

X-ray imaging devices have been commonly used in regular modem medical examinations. In addition to fixed X-ray imaging devices, there are also movable X-ray machines that are designed for easy use in multiple environments. The movable X-ray machines help prevent a patient who is heavily sick or has difficult in moving from being moved between wards and an examination chamber for photographing in order to reduce any potential damage caused during the patient being moved or any potential risk to the lives of people who are heavily ill.

A conventional movable X-ray imaging device, although having a size and weight that are smaller than a fixed device, requires complicated accessories and thus has quite a weight and size, which greatly affect the flexibility and efficiency of moving. An operator, when moving an X-ray imaging device, is easy to have the eyesight blocked by the bulky size and it is even much easier for controlling the device being difficult due to the great weight thereof so that it is generally hard to tell if a person or an obstacle existing in front thereof and it is often impossible to immediately stop or change direction because of the difficult control resulting from the heavy weight upon realizing such existence of the person or obstacle. The X-ray machines are generally of high prices and expenditure for repairing is expensive once the machine gets damaged duo to collision. In addition, it is even worse if a person or a child standing in front is hit and hurt.

Further, a movable X-ray imaging device is generally used in hospitals or clinics. Large-sized hospitals have the highest frequency of using the device. However, for a large-sized hospital, there are usually a large number of departments, diagnosis rooms, and wards, in addition to examination chambers, surgery rooms, and treatment rooms, where X-ray machines are necessarily used. There are also a lot of people walking and moving in a large-sized hospital, so that if an operator is not familiar with a specific moving route or the entire environment, it is possible to have the movement of X-ray equipment to a correct site severely delayed, affecting timely treatments of patients. Another situation would be that movement to an incorrect inspection site may result, leading to incorrect photographing of patients. This may even cause erroneous treatments.

To help an operator to move an X-ray imaging device along a correct path in an efficient, quick, and safe manner, it becomes an issue of development and research of those involved in the field to provide a solution that overcomes the above problems of the known devices.

SUMMARY OF THE INVENTION

Thus, to overcome the above problems, an object of the present invention is to provide an environment recognition guide system of a movable medical equipment, which through combining an environment recognition guide system with a movable medical equipment, overcomes the inconvenience of an operator moving a movable medical equipment and also reduces the operation time thereof and enhances safety and correctness of operation.

Another object of the present invention is to provide a movable medical equipment comprising an assistive guide moving system, which determines if the movable medical equipment be advanced by first acquiring an environment image pixel depth signal of a preset guide path existing in an environmental space, followed by comparison with a pre-stored predetermined object image pixel depth signal.

A further object of the present invention is to provide a movable medical equipment with collision protection function to prevent the medical equipment from collision with a front obstacle during the movement.

To achieve the above objects, the technical solution adopted in the present invention is that a movable medical equipment is combined with an environment recognition guide system, which comprises an environment data storage device and an object image recognition device, both being connected to a processor unit, the environment data storage device being loaded with predetermined object image pixel depth signals of a plurality of objects existing along a preset guide path in an environmental space. The object image recognition device compares an environment image pixel depth signal with the predetermined object image pixel depth signals loaded in the environment data storage device for recognition. When the environment image pixel depth signal is determined matching the predetermined object image pixel depth signals, a movement control signal is generated and applied to the motor control circuit to allow the motor control circuit to control the driving motor to operate for driving the medical equipment to move along the preset guide path.

The environment recognition guide system may further comprise an image capture device and a display device.

The predetermined object image pixel depth signals comprise an image pixel depth signal of one of a wall, a column, a corner and a projection of a building and may also comprise one of a room number and an identification tag of a room.

The environment recognition guide system may further comprise an alarm device.

The environment recognition guide system may further comprise a distance determination device connected to the processor unit. The processor unit, upon receiving an obstacle image pixel depth signal acquired by the depth camera, computes an obstacle distance between the depth camera and the obstacle that is transmitted to the distance determination device, so that when the distance determination device determines the obstacle distance is greater than a safe distance reference value, a movement control signal is generated and applied to the driving motor of the medical equipment to control the driving motor to operate normally. If the distance determination device determines the obstacle distance is less than a deceleration distance reference value, a deceleration control signal is generated to control the driving motor to decelerate.

If the distance determination device determines the obstacle distance is less than a stop distance reference value, a stop control signal s generated to control the driving motor to stop.

As to the efficacy, with the above-discussed technical solution adopted in the present invention, when moving an X-ray medical equipment, an operator can be assisted through guidance provided by the environment recognition guide system of the present invention to easily realize the path leading to a destination so that the inconvenience that an operator, when moving a medical equipment, is not familiar with the environment can be overcome and the operation time can be generally reduced and the safety of movement can be enhanced.

Further, when the X-ray medical equipment is being moved, the obstacle determination function may help to achieve collision protection.

BRIEF DESCRIPTION OF THE DRAWINGS

The present invention will be apparent to those skilled in the art by reading the following description of preferred embodiments of the present invention, with reference to the attached drawings, in which:

FIG. 6 illustrating a corresponding relationship of control signals and medical equipment moving modes for the movable medical equipment at different obstacle distances according to the second embodiment of the present invention;

DETAILED DESCRIPTION OF THE PREFERRED EMBODIMENTS

Figure 1:
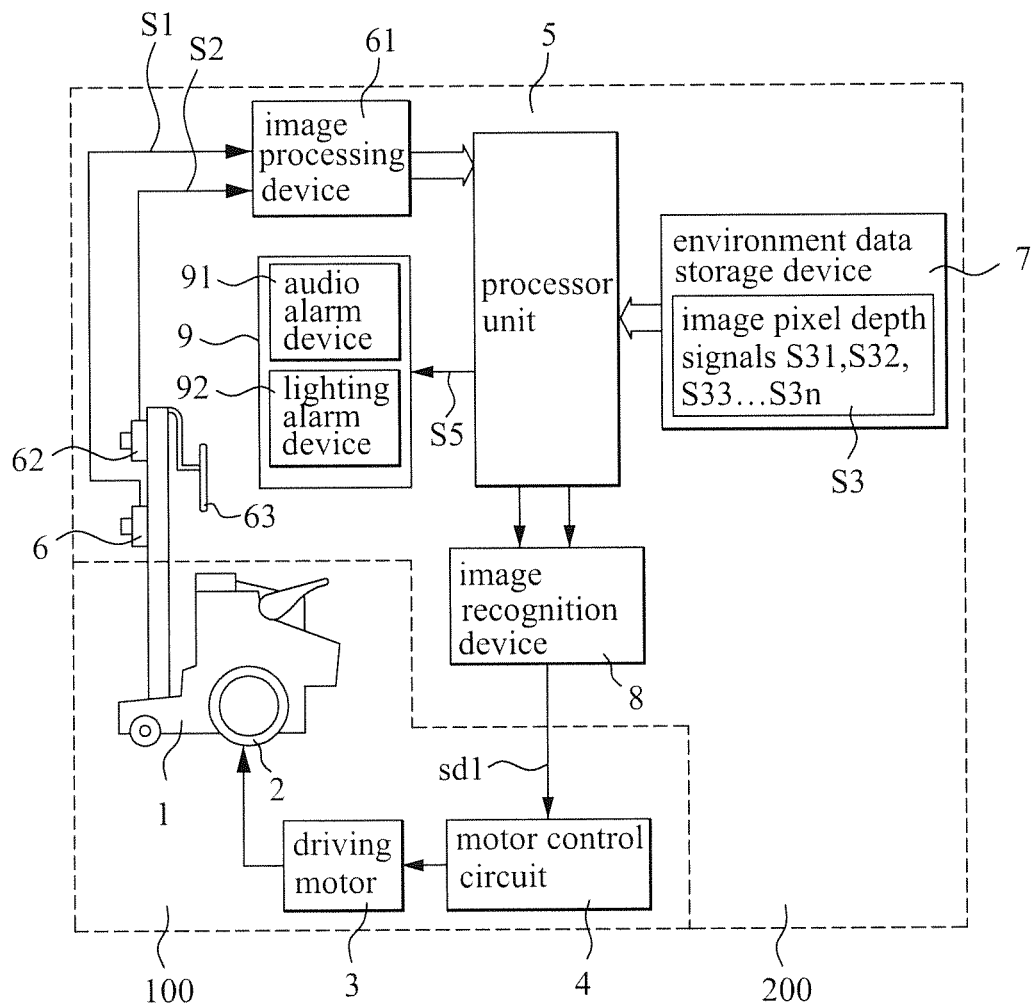
FIG. 1 is a schematic view showing a circuit system of an environment recognition guide system of a movable medical equipment in according to a first embodiment of the present invention.

With reference to the drawings and in particular to FIG. 1, an illustration is given to show a medical equipment 100 according to the present invention comprises a movable carrier 1 on which a wheel 2, a driving motor 3, and a motor control circuit 4 are mounted. The driving motor 3 is connected to the motor control circuit 4. Under the operation of a user, the motor control circuit 4 controls the driving motor 3 to operate in order to drive the wheel 2 to make the movable carrier 1 of the medical equipment 100 to move in a moving direction M1 along a preset guide path L in an environmental space P.

In the present invention, an environment recognition guide system 200 is included and combined with the medical equipment 100, so that the environment recognition guide system 200 operates the motor control circuit 4 of the medical equipment 100 to control the operation of the driving motor 3.

The environment recognition guide system 200 according to the present invention comprises a processor unit 5, a depth camera 6, an environment data storage device 7, and an object image recognition device 8. The depth camera 6 is connected via an image processing device 61 to the processor unit 5 and the depth camera 6 is disposed at a front location of the medical equipment 100 that faces the moving direction M1 in order to acquire an environment image pixel depth signal S1 existing in front of the medical equipment 100.

The environment data storage device 7 is connected to the processor unit 5 and stores therein predetermined object image pixel depth signals S31, S32, S33, . . . , S3n of a plurality of objects A1, A2, A3, . . . , An that is predetermined to exist along the preset guide path L in the environmental space P. Corresponding relationship among the preset guide path L, the objects A1, A2, A3, . . . , An, and the predetermined object image pixel depth signals S31, S32, S33, . . . , S3n is referred to what shown in FIG. 2.

The object image recognition device 8 is connected to the processor unit 5 for comparison of the environment image pixel depth signal S1 acquired by the depth camera 6 with the predetermined object image pixel depth signals 63 stored in the environment data storage device 7 for recognition.

When the environment image pixel depth signal S1, after the comparison, matches the predetermined object image pixel depth signals S3, a movement control signal sd1 is generated and applied to the motor control circuit 4, so that the motor control circuit 4 controls the driving motor 3 to operate for driving the medical equipment 100 to move along the preset guide path L.

Figures 2, 3:
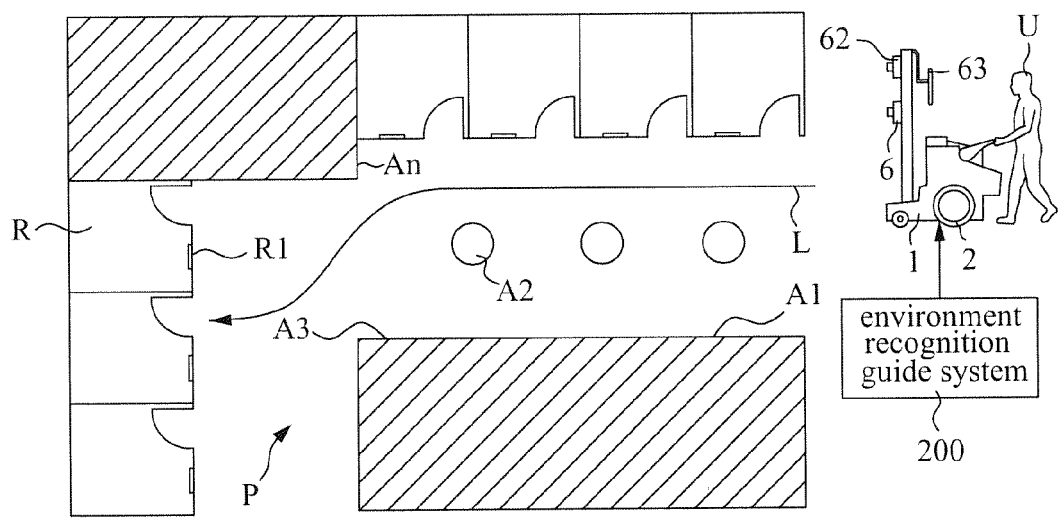
FIG. 2 illustrating a corresponding relationship of predetermined object image pixel depth signals of objects existing in a preset guide path according to the first embodiment of the present invention.
FIG. 3 is a schematic view illustrating a medical equipment moving along a preset guide path according to the first embodiment of the present invention.

FIG. 3 is a schematic view illustrating the medical equipment 100 moving along a preset guide path L in the environmental space P. The drawing illustrates under the operation of an operator, the medical equipment 100 moves forward along the preset guide path L in the environmental space P. At the same time when the movement is being carried out, the depth camera 6 constantly acquires an environment image pixel depth signal S1 of an object A1, A2, A3, . . . , An (such as a wall, a column, a corner, a projection of a building in the environmental space P) along the preset guide path L to perform an immediate comparison operation. After comparison, when the environment image pixel depth signal S1 is determined matching the predetermined object image pixel depth signals S3, a movement control signal sd1 is normally generated and applied to the motor control circuit 4 to allow the motor control circuit 4 to control the driving motor 3 to operate in order to drive the medical equipment 100 to move along the preset guide path L.

The processor unit 5 is also connected with an alarm device 9. The alarm device 9 may comprise an audio alarm device 91 and a lighting alarm device 92. When the environment image pixel depth signal SI is compared with and determined not matching the predetermined object image pixel depth signals 93, no movement control signal sd1 is generated so that the medical equipment 100 is not driven to move forward. Under such a condition, the processor unit 5 generates an alarm signal 85 to the alarm device 9 to timely give off sound or light alarms.

Further, the objects that exist along the preset guide path L may also comprise a room number R1 or an identification tag of a room R in the environmental space P. The object image recognition device 8 according to the present invention may recognize the room number R1 or the identification tag of a room R in order to determine if it is a correct target site.

Referring to FIG. 1 again, the present invention may further comprise an image capture device 62, which is connected via the image processing device 61 to the processor unit 5. The image capture device 62 is disposed at a front location of the medical equipment 100 facing the moving direction M1 in order to capture an instant image S2 of an object A1, A2, A3, ..., An along the preset guide path L in front of the medical equipment 100.

The image capture device 62 is also connected to a display device 63 and the display device 63 is arranged at a location on the movable carrier 1 at the rear side of the medical equipment 100 in the moving direction (namely in the direction facing the user). As such, a user, when pushing the medical equipment 100 forward, may watch the instant image in front of the movable carrier 1 by means of the display device 63.

Figure 4:
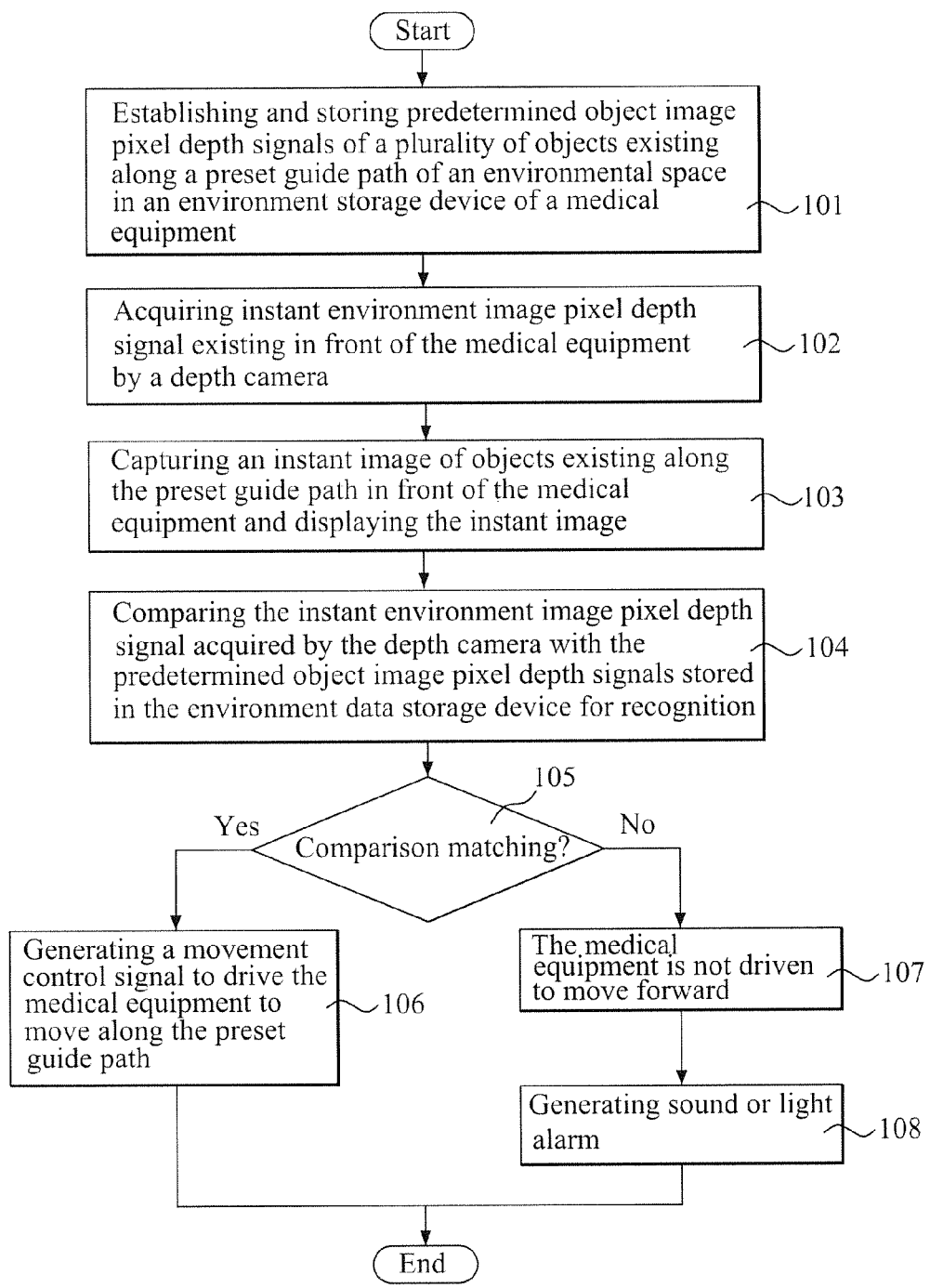
FIG. 4 is a control flow chart of the first embodiment of the present invention.

FIG. 4 shows a control flow chart. Additional reference is made to FIGS. 1-3 for an illustration of a control flow of the present invention. When the present invention is performing an assisted guide function, steps comprise first establishing and storing predetermined object image pixel depth signals S31, S32, S33, ..., S3n of a plurality of objects A1, A2, A3, ..., An which exist along a preset guide path R of an environmental space P in an environment data storage device 7 of an environment recognition guide system 100 (Step 101).

When an operator pushes the medical equipment 100 to move forward along the preset guide path R, a depth camera 6 arranged on the environment recognition guide system 200 of the present invention instantaneously acquires an environment image pixel depth signal S1 existing in front of the medical equipment 100 (Step 102) and transmits the environment image pixel depth signal S1 to a processor unit 5.

At the same time, an image capture device 62 may also be operated to capture an instant image S2 of an object A1, A2, A3,..., An which exist along the preset guide path L in front of the medical equipment 100 and a display device 63 may be used to display the instant image S2 (Step 103).

An object image recognition device 8 compares the environment image pixel depth signal S1 acquired by the depth camera 6 with the predetermined object image pixel depth signals S3 stored in the environment data storage device 7 for recognition (Step 104).

When the environment image pixel depth signal S1, after the comparison, is determined matching the predetermined object image pixel depth signals S3 (Step 105), a movement control signal sd1 is generated and applied to a motor control circuit 4 to allow the motor control circuit 4 to control the driving motor 3 to operate in order to drive the medical equipment 100 to move along the preset guide path L (Step 106).

When the environment image pixel depth signal S1, after comparison, is determined not matching the predetermined object image pixel depth signals S3, no movement control signal sd1 is generated so that the medical equipment 100 is not driven to move forward (Step 107). Under such a condition, a sound or light alarm may be issued (Step 108).

Figure 5:
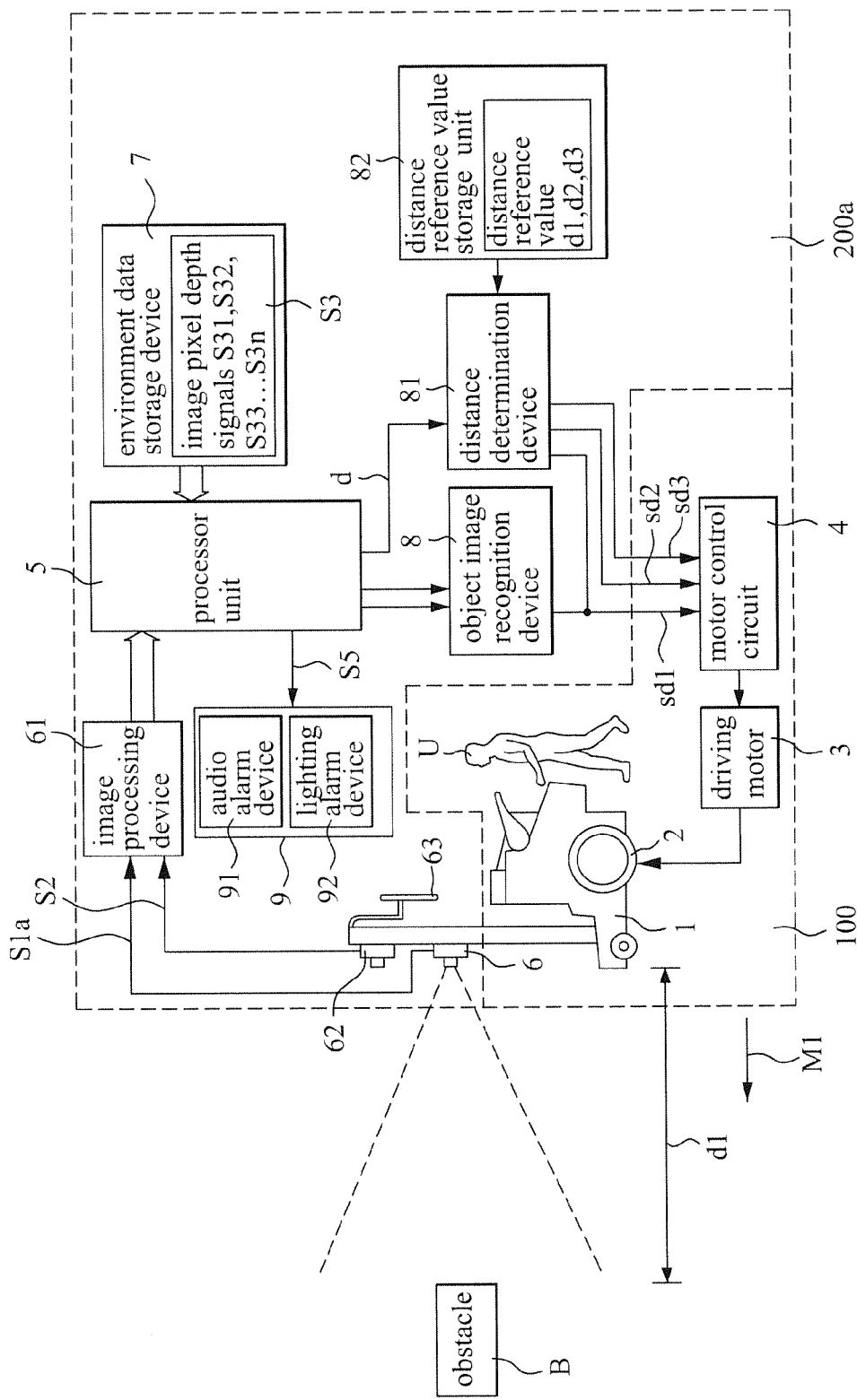
FIG. 5 is a schematic view showing a circuit system of an environment recognition guide system of a movable medical equipment in according to a second embodiment of the present invention.

FIG. 5 is a schematic view showing a circuit system of an environment recognition guide system of a movable medical equipment in according to a second embodiment of the present invention. The instant embodiment is made up of constituent components that are substantially identical to those of the first embodiment illustrated in FIG. 1 and a difference resides in that the environment recognition guide system 200a of the instant embodiment further comprises a distance determination device 81 that is connected to a processor unit 5 and a distance reference value storage unit 82. The distance reference value storage unit 82 stores therein a safe distance reference value d1, a deceleration distance reference value d2, and a stop distance reference value d3. With the second embodiment of the present invention, collision protection can be achieved.

When the medical equipment 100 is moved in a moving direction M1, if an obstacle B is present in the front, a depth camera 6 supplies an obstacle image depth signal S1a of the obstacle B through an image processing device 61 to the processor unit 5 to allow the processor unit 5 to compute, according to the obstacle image depth signal S1a, an obstacle distance d between the depth camera 6 and the obstacle B that is transmitted to a distance determination device 7.

FIG. 6 illustrates a corresponding relationship between control signals associated with different obstacle distances of the movable medical equipment of the present invention and moving modes of the medical equipment. The distance determination device 81, upon receiving the obstacle distance d, compares the obstacle distance d with distance reference values d1, d2, d3 set in the distance reference value storage unit 71.

When the distance determination device 81 determines the obstacle distance d is greater than the safe distance reference value d1 of the distance reference values, a normal movement control signal sd1 is generated and applied to the motor control circuit 4 of the medical equipment 100 to allow the motor control circuit 4 to control the driving motor 3 to move forward normally.

Figure 7:
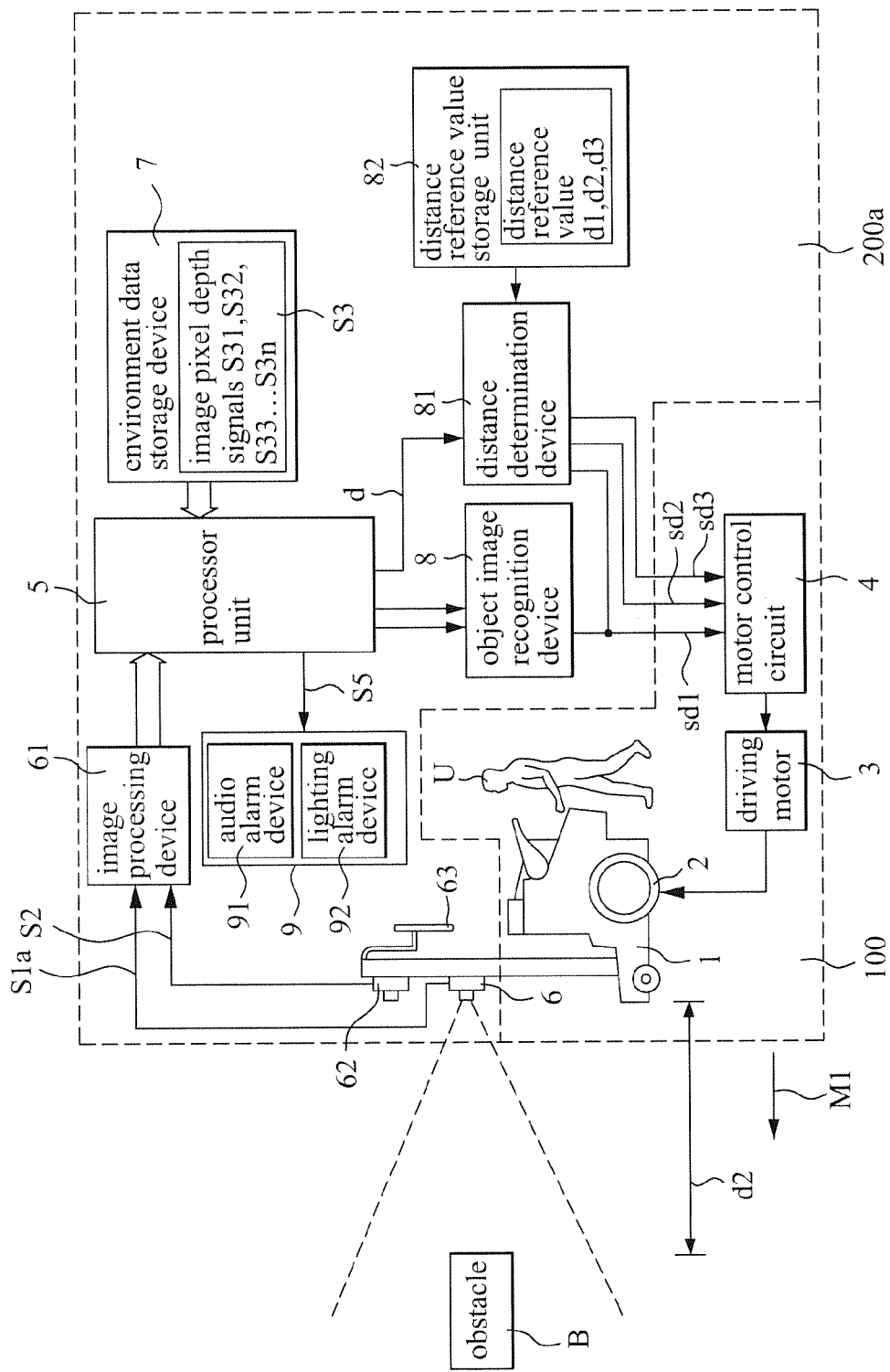
FIG. 7 is a schematic view showing the circuit system of the movable medical equipment according to the second embodiment of the present invention in a situation of reducing speed.

As shown in FIG. 7, when the distance determination device 81 determines the obstacle distance d is less than the deceleration distance reference value d2 of the distance reference values, a deceleration control signal sd2 is generated and applied to the motor control circuit 4 of the medical equipment 100 to allow the motor control circuit 4 to control the driving motor 3 to reduce speed.

Figure 8:
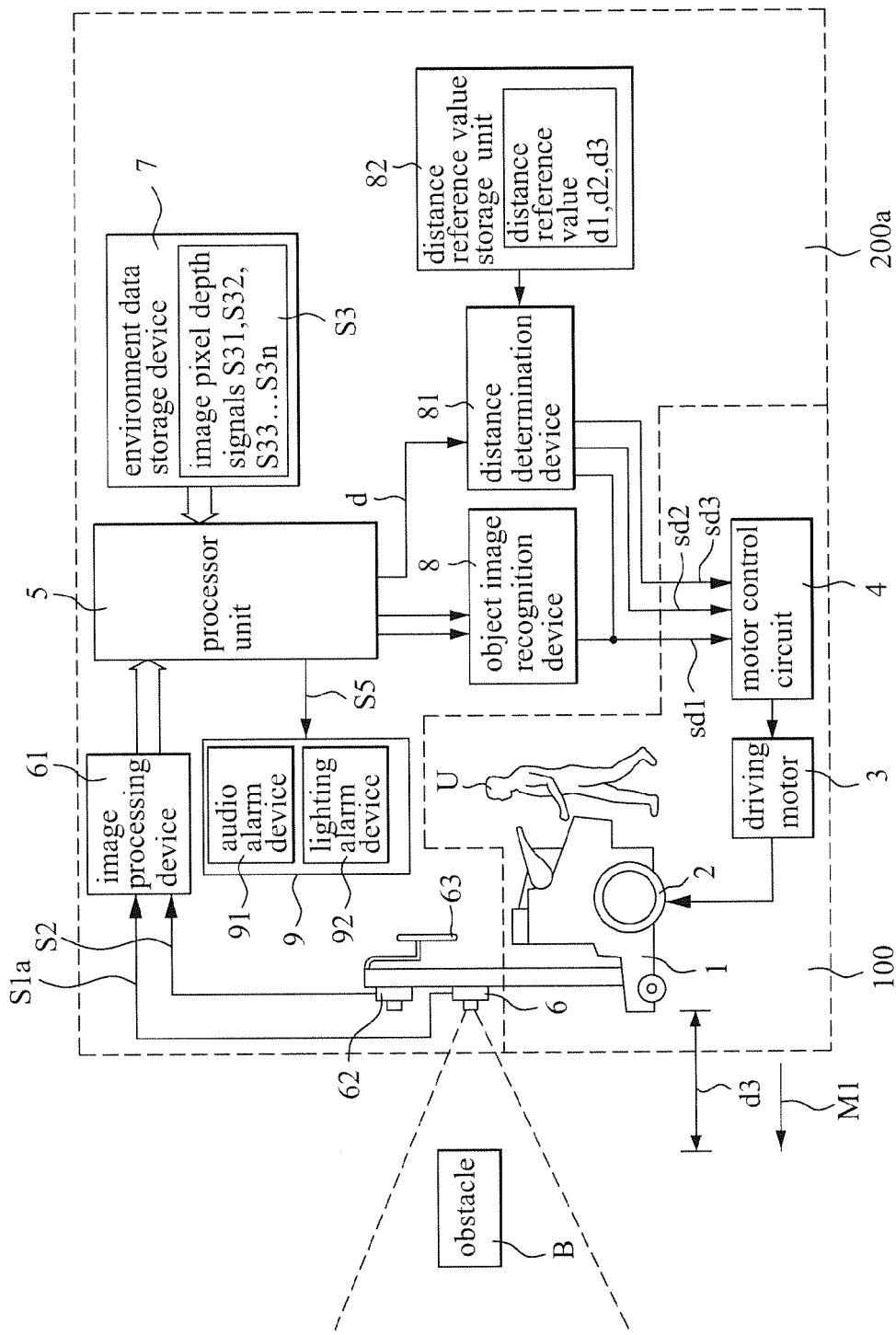
FIG. 8 is a schematic view showing the circuit system of the movable medical equipment according to the second embodiment of the present invention in a situation of being stopped.

As shown in FIG. 8, when the distance determination device 81 determines the obstacle distance d is less than the stop distance reference value d3 of the distance reference values, a stop control signal sd3 is generated and applied to the motor control circuit 4 of the medical equipment 100 to allow the motor control circuit 4 to control the driving motor 3 to stop operation.

In addition to the above-mentioned he deceleration control signal sd2 and the stop control signal sd3, the distance determination device 81 may also generate and apply an alarm signal S5 to an alarm device 9 for giving off an alarm in the form of sound of light.

Although the present invention has been described with reference to the preferred embodiments, it is apparent to those skilled in the art that a variety of modifications and changes may be made without departing from the scope of the present invention which is intended to be defined by the appended claims.

What is claimed is:

1. An environment recognition guide system for a movable medical equipment, the medical equipment comprising a movable carrier on which at least a wheel, a driving motor, and a motor control circuit are disposed, wherein the motor control circuit is connected to the driving motor and the motor control circuit controls the driving motor to operate for driving the wheel to cause the movable carrier of the medical equipment to move forward in a moving direction along a preset guide path in an environmental space, the environment recognition guide system comprising:

a processor unit;

a depth camera, which is connected via an image processing device to the processor unit, the depth camera being arranged at a front position of the medical equipment facing the moving direction in order to acquire an environment image pixel depth signal existing in front of the medical equipment;

an environment data storage device, which is connected to the processor unit and stores therein predetermined object image pixel depth signals of a plurality of objects existing along the preset guide path in the environmental space;

an object image recognition device, which is connected to the processor unit to compare the environment image pixel depth signal acquired by the depth camera with the predetermined object image pixel depth signals stored in the environment data storage device for comparison;

a distance determination device, which is connected to the processor unit; and a distance reference value storage unit, which is connected to the distance determination device and stores therein a safe distance reference value, a deceleration distance reference value, and a stop distance reference value;

wherein when the processor unit receives the environment image pixel depth signal acquired by the depth camera, the object image recognition device compares the environment image pixel depth signal with the predetermined object image pixel depth signals stored in the environment data storage device for recognition;

when the environment image pixel depth signal is determined matching the predetermined object image pixel depth signals, a movement control signal is generated and applied to the motor control circuit to allow the motor control circuit to control the driving motor to operate for driving the medical equipment to move along the preset guide path;

the depth camera captures an obstacle image pixel depth signal of an obstacle existing in front of the medical equipment; and the processor unit, upon receiving the obstacle image pixel depth signal of the depth camera, computes an obstacle distance between the depth camera and the obstacle that is transmitted to the distance determination device, so that the distance determination device, upon determining the obstacle distance is greater than the safe distance reference value, generates and applies the movement control signal to the motor control circuit to allow the motor control circuit to control the driving motor to operate.

2. The environment recognition guide system as claimed in claim 1 further comprising an image capture device, which is connected via the image processing device to the processor unit, the image capture device being arranged at a front position of the medical equipment facing the moving direction in order to capture an instant image of an object existing in front of the medical equipment along the preset guide path.

3. The environment recognition guide system as claimed in claim 2 further comprising a display device, which is connected to the image capture device, the display device being arranged on the medical equipment at a location at a rear side of the medical equipment in the moving direction.

4. The environment recognition guide system as claimed in claim 1, wherein the predetermined object image pixel depth signals comprise an image pixel depth signal of one of a wall, a column, a corner, and a projection of a building in the environmental space.

5. The environment recognition guide system as claimed in claim 1, wherein the predetermined object image pixel depth signals comprise an image pixel depth signal of one of a room number and an identification tag of a room.

6. The environment recognition guide system as claimed in claim 1 further comprising an alarm device connected to the processor unit.

7. The environment recognition guide system as claimed in claim 1, wherein the distance determination device, upon determining the obstacle distance is less than the deceleration distance reference value, generates and applies a deceleration control signal to the motor control circuit to allow the motor control circuit to control the driving motor to decelerate.

8. The environment recognition guide system as claimed in claim 1, wherein the distance determination device, upon determining the obstacle distance is less than the stop distance reference value, generates and applies a stop control signal to the motor control circuit to allow the motor control circuit to control the driving motor to stop.

* * * * *